United States Patent [19]
Campbell, Jr. et al.

[11] Patent Number: 6,150,297
[45] Date of Patent: Nov. 21, 2000

[54] CYCLOPENTAPHENANTHRENYL METAL COMPLEXES AND POLYMERIZATION PROCESS

[75] Inventors: Richard E. Campbell, Jr.; Francis J. Timmers; Ravi B. Shankar; Daniel J. Arriola, all of Midland, Mich.

[73] Assignee: The Dow Chemical Company, Midland, Mich.

[21] Appl. No.: 09/122,958

[22] Filed: Jul. 27, 1998

Related U.S. Application Data

[60] Provisional application No. 60/059,000, Sep. 15, 1997.

[51] Int. Cl.[7] .............................. B01J 31/02; B01J 31/18; C08F 4/44
[52] U.S. Cl. ..................... 502/152; 502/155; 526/133; 526/134; 526/160; 526/161; 526/348.6; 526/347
[58] Field of Search ...................... 502/108, 116, 502/117, 155, 152; 526/116, 943, 160, 161, 133, 134

[56] References Cited

U.S. PATENT DOCUMENTS 5,932,669  8/1999  Rohrmann et al. ................. 526/160

FOREIGN PATENT DOCUMENTS 197 25 647 A1  12/1998  Germany ........................ 502/108

OTHER PUBLICATIONS

Schneider et al., ansa–Zirconocene Complexes with Modified Benzindenyl Ligands: Synthese, Crystal Structure, and Properties as Propene Polymerization Catalysts, Organometallics 16 (15), 3413–3420, Jul. 1997.

Schneider et al., Cyclopenta[1]phenathrene titanium trichloride derivatives: syntheses, crystal structure and properties as catalysts for styrene polymerization, JOMC 545–546, (Oct. 1997) 291–295.

Primary Examiner—David W. Wu
Assistant Examiner—R. Harlan

[57] ABSTRACT

Group 4 metal complexes comprising a cyclopentaphenanthreneyl ligand, catalytic derivatives thereof and their use as olefin polymerization catalysts, especially for the copolymerization of ethylene and a vinylaromatic monomer are disclosed. The resulting copolymers are uniform, pseudo-random copolymers of ethylene and a vinylaromatic monomer having a cluster index, $CI_{ES}$ less than 1.0 and a polymerized vinylaromatic monomer content less than 50 mole percent.

8 Claims, 2 Drawing Sheets

CYCLOPENTAPHENANTHRENYL METAL COMPLEXES AND POLYMERIZATION PROCESS

CROSS-REFERENCE TO RELATED APPLICATION

This application claims benefit of priority from provisional application Ser. No. 60/059,000, filed Sep. 15, 1997, the teachings of which are incorporated herein by reference.

BACKGROUND OF THE INVENTION

This invention relates to a class of Group 4 metal complexes and to polymerization catalysts derived therefrom that are particularly suitable for use in a polymerization process for preparing homopolymers and copolymers of olefins or diolefins, including copolymers comprising two or more olefins or diolefins such as copolymers comprising a monovinyl aromatic monomer and ethylene. In addition, the catalysts uniquely prepare new polymeric products having desirable physical properties.

Constrained geometry metal complexes and methods for their preparation are disclosed in U.S. Pat. No. 5,703,187. This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. Pat. Nos. 5,321,106; 5,721,185, 5,374,696, 5,470,993, 5,541,349, and 5,486,632, as well as WO97/15583, and WO97/19463. The teachings of all of the foregoing patents or the corresponding equivalent U.S. patent applications are hereby incorporated by refer

SUMMARY OF THE INVENTION

Figure 1:
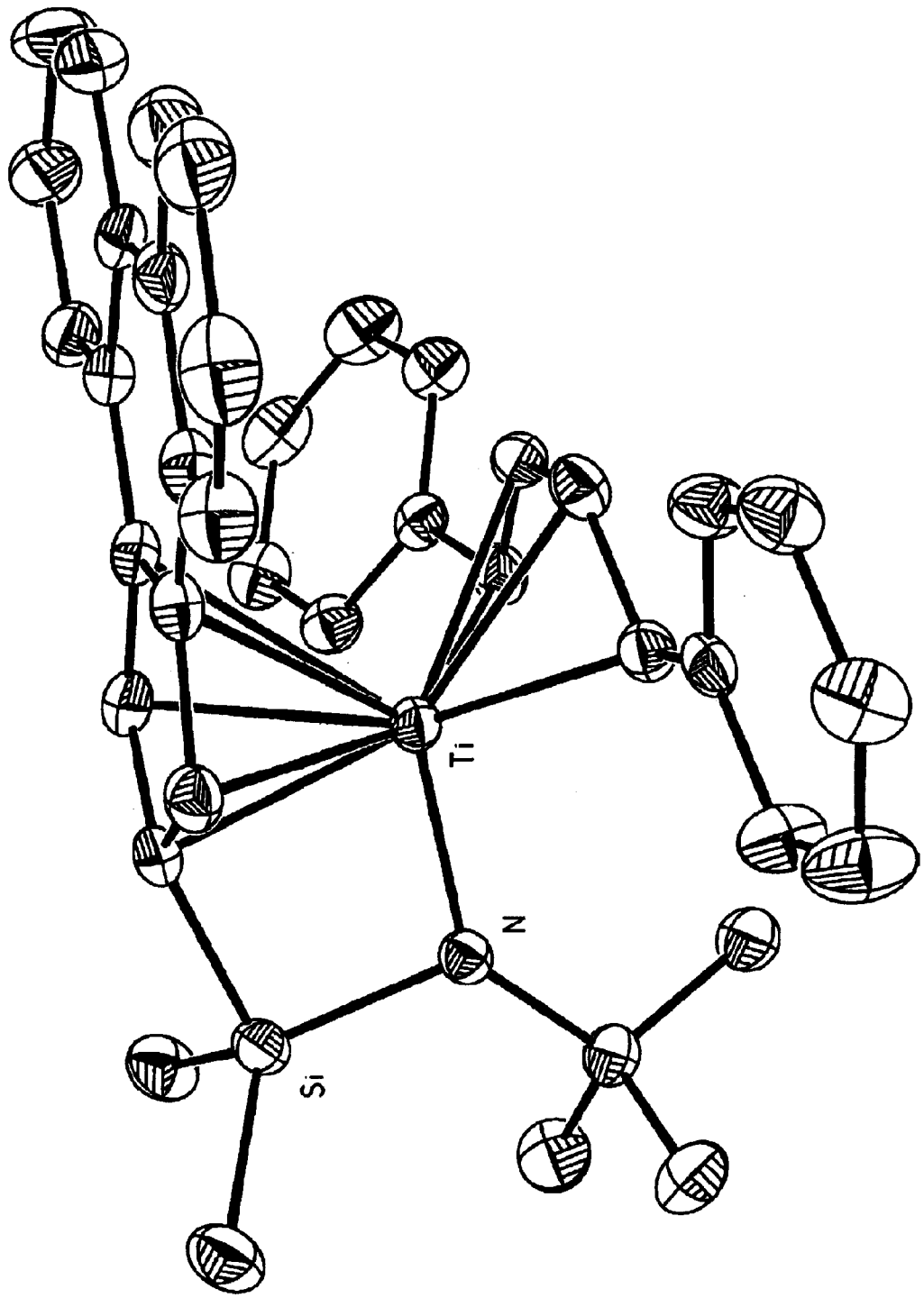
FIG. 1 is an ORTEP drawing based on single crystal X-ray data of the compound of Example 3.

According to the present invention there are provided metal complexes corresponding to the formula: $CpZMX_xL_lX'_{x'}$ (IA);

where Cp is a cyclopentaphenanthrenyl ring system ligand optionally substituted with one or more ligand groups selected from hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylenephosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl ligand groups, said ligand group having up to 40 atoms not counting hydrogen atoms, and optionally two or more of the foregoing ligand groups may together form a divalent derivative, and further optionally one or more carbons of the cyclopentaphenanthrenyl ring system may be replaced by a nitrogen or phosphorus atom;

M is titanium, zirconium or hafnium in the +2, +3 or +4 formal oxidation state;

Z is either a cyclic or noncyclic ligand group containing delocalized π-eletrons, including a second cyclopentaphenanthrenyl ring system group as herein previously disclosed for Cp, said Z being bonded to M by means of delocalized π-electrons and optionally covalently bonded to Cp through a divalent bridging group, or Z is a divalent moiety lacking in delocalized π-electrons that is covalently bonded to Cp and M, or such a moiety comprising one σ-bond by which it is bonded to Cp, and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms other than hydrogen;

L independently each occurrence is a neutral ligating compound having up to 20 atoms;

X' is a divalent anionic ligand group having up to 60 atoms;

x is 0, 1, 2, or 3;

l is a number from 0 to 2, and x' is 0 or 1.

The above complexes may exist as isolated crystals optionally in pure form, or as a mixture with other complexes, in the form of a solvated adduct, optionally in a solvent, especially an organic liquid, as well as in the form of a dimer or chelated derivative thereof, wherein the chelating agent is an organic material such as ethylenediaminetetraacetic acid (EDTA).

Also, according to the present invention, there is provided a catalyst for olefin polymerization comprising:

A. 1) a metal complex of formula (IA), and
   2) an activating cocatalyst, the molar ratio of 1) to 2) being from 1:10,000 to 100:1, or B. the reaction product formed by converting a metal complex of formula (IA) to an active catalyst by use of an activating technique.

Further according to the present invention there is provided a process for the polymerization of olefins comprising contacting one or more $C_{2-20}$ α-olefins under polymerization conditions with a catalyst comprising:

A. 1) a metal complex of formula (IA), and
   2) an activating cocatalyst, the molar ratio of 1) to 2) being from 1:10,000 to 100:1, or B. the reaction product formed by converting a metal complex of formula (IA) to an active catalyst by use of an activating technique.

Use of the present catalysts and processes is especially efficient in production of olefin homopolymers, copolymers of two or more olefins, in particular, copolymers of ethylene and a vinylaromatic monomer, such as styrene, and interpolymers of three or more polymerizable monomers over a wide range of polymerization conditions, and especially at elevated temperatures. They are especially useful for the formation of ethylene homopolymers, copolymers of ethylene and one or more higher X-olefins (i. e., olefins having 3 or more carbon atoms), copolymers of ethylene, propylene and a diene (EPDM copolymers), copolymers of ethylene and vinylaromatic monomers such as styrene (ES polymers), copolymers of ethylene, styrene, and a diene (ESDM polymers), and copolymers of ethylene, propylene and styrene (EPS polymers). Examples of suitable diene monomers include ethylidenenorbornene, 1,4-hexadiene or similar conjugated or nonconjugated dienes.

The ES polymers generated using certain of the present catalyst compositions are additionally remarkable due to the fact that they possess a novel physical structure characterized by regular, homogeneous incorporation of vinylaromatic monomer into the polymer chain, compared to conventional ES polymers in which the vinylaromatic monomer tends to be incorporated in clusters of alternating comonomers. Such polymers possess lower peak melting points and glass transition temperatures (Tg) at comparable compositions, polymer molecular weights and molecular weight distributions compared to previously known ES polymers.

The catalysts of this invention may also be supported on a support material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

DETAILED DESCRIPTION

All reference to the Periodic Table of the Elements herein shall refer to the Periodic Table of the Elements, published and copyrighted by CRC Press, Inc., 1995. Also, any reference to a Group or Groups shall be to the Group or Groups as reflected in this Periodic Table of the Elements using the IUPAC system for numbering groups.

Cyclopentaphenanthreneyl ring system ligands, Cp, occur in several isomeric arrangements of the various rings, conventionally indicated by use of an italicized letter in the name. All of the known non-equivalent isomeric forms (indicated as the a, b, c and l forms) are suitable for use herein. Preferred cyclopentaphenanthrenyl ring system ligand are those base on cyclopenta[c]phenanthreneyl or cyclopenta[l]phenanthrenyl groups.

Preferred metal complexes according to the present invention correspond to the formula are 1H-cyclopenta[l]-phenanthreneyl metal complexes corresponding to the formula:

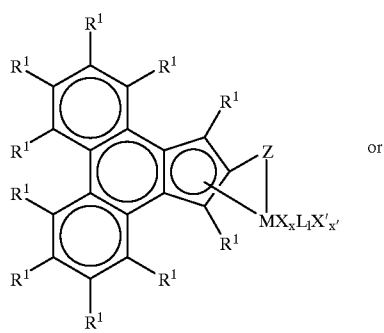

(IB)

or

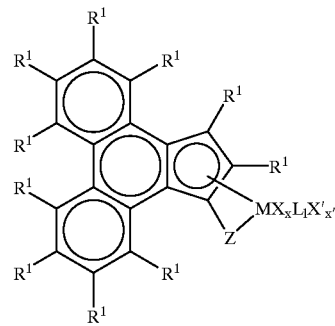

-continued (IC)

where M is titanium, zirconium or hafnium in the +2, +3 or +4 formal oxidation state;

$R^1$ independently each occurrence is hydrogen, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said $R^1$ group having up to 40 atoms not counting hydrogen atoms, and optionally two or more of the foregoing adjacent $R^1$ groups may together form a divalent derivative thereby forming a saturated or unsaturated fused ring, and further optionally one or more of the carbons of any of the rings may be replaced by a nitrogen or sulfur atom;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized 7electrons;

L independently each occurrence is a neutral ligating compound having up to 20 atoms;

X' is a divalent anionic ligand group having up to 60 atoms;

x is 0, 1, 2,or 3;

l is a number from 0 to 2, and x' is 0 or 1.

In the metal complexes, preferred L groups are carbon monoxide; phosphines, especially trimethylphosphine, triethylphosphine, triphenylphosphine and bis(1,2-dimethylphosphino)ethane; $P(OR^4)_3$, wherein $R^4$ is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms. Complexes including such neutral diene L groups are those wherein the metal is in the +2 formal oxidation state.

Further in reference to the metal complexes, X preferably is selected from the group consisting of hydro, halo, hydrocarbyl, silyl, and N,N-dialkylamino-substituted hydrocarbyl. The number of X groups depends on the oxidation state of M, whether Z is divalent or not and whether any neutral diene groups or divalent X' groups are present. The skilled artisan will appreciate that the quantity of the various substituents and the identity of Z are chosen to provide charge balance, thereby resulting in a neutral metal complex. For example, when Z is divalent, and x is zero, x' is two less than the formal oxidation state of M. When Z contains one neutral two electron coordinate-covalent bonding site, and M is in a formal oxidation state of +3, x may equal zero and x' equal 1, or x may equal 2 and x' equal zero. In a final example, if M is in a formal oxidation state of +2, Z may be a divalent ligand group, whereupon x and x' are both equal to zero and one neutral L ligand group may be present.

Cyclopentaphenanthreneyl ligands are known ligands or may be readily prepared from known compounds by one skilled in the art, using published techniques or techniques analogous to published techniques. For example, 1H-cyclopenta[l]phenanthrene which corresponds to the formula:

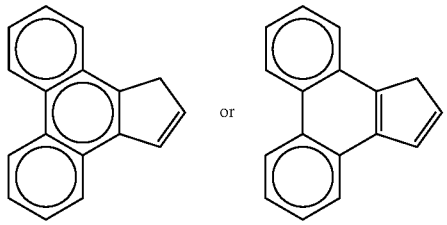

is a known compound. It, as well as the corresponding lithium salt, 1H-cyclopenta[l]-phenanthrene-2-yl, were disclosed in *J. Org. Chem.* (54), 171–175 (1989).

More preferred cyclopentaphenanthrenyl ring system ligand metal complexes used according to the present invention are 1H-cyclopenta[l]phenanthrene-2-yl complexes corresponding to the formula:

(ID)

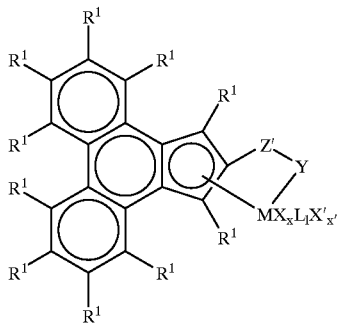

wherein:

M is titanium;

$R^1$ each occurrence is hydrogen or a hydrocarbyl, amino or amino-substituted hydrocarbyl group of up to 20 atoms other than hydrogen;

Y is —O—, —S—, —$NR^5$—, —$PR^5$—; —$NR^5_2$, or —$PR^5_2$;

Z' is $SiR^5_2$, $CR^5_2$, $SiR^5_2SiR^5_2$, $CR^5_2CR^5_2$, $CR^5=CR^5$, $CR^5_2SiR^5_2$, $BR^5$, or $GeR^5_2$;

$R^5$ each occurrence is independently hydrogen, or a member selected from hydrocarbyl, hydrocarbyloxy, silyl, halogenated alkyl, halogenated aryl, and combinations thereof, said $R^5$ having up to 20 non-hydrogen atoms, and optionally, two $R^5$ groups from Z' (when $R^5$ is not hydrogen), or an $R^5$ group from Z' and an $R^5$ group from Y form a ring system;

X, L, and X' are as previously defined;

x is 0, 1 or 2;

l is 0 or 1; and x' is 0 or 1;

with the proviso that:

when x is 2, x' is zero, M is in the +4 formal oxidation state (or M is in the +3 formal oxidation state if Y is —$NR^5_2$ or —$PR^5_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen, when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms, when x is 1, and x' is 0, M is in the +3 formal oxidation state, and X is a stabilizing anionic ligand group selected from the group consisting of allyl, 2-(N,N-dimethylamino)phenyl, 2-(N,N-dimethylaminomethyl) phenyl, and 2-(N,N-dimethylamino)benzyl, and when x and x' are both 0, l is 1, M is in the +2 formal oxidation state, and L is a neutral, conjugated or nonconjugated diene, optionally substituted with one or more hydrocarbyl groups, said L having up to 40 carbon atoms and being bound to M by means of delocalized π-electrons thereof.

Most preferred metal complexes are those according to the previous formula (ID), wherein M, R', X, L, X', Z', Y, x, l and x' are as previously defined, with the proviso that:

when x is 2, l and x' are both zero, M is in the +4 formal oxidation state, and X is independently each occurrence methyl, benzyl, or halide;

when x and l are zero, x' is one, and M is in the +4 formal oxidation state, X' is a 1,4-butadienyl group that forms a metallocyclopentene ring with M, when x is 1, l and x' are zero, M is in the +3 formal oxidation state, and X is 2-(N,N-dimethylamino) benzyl; and when x and x' are 0, l is 1, M is in the +2 formal oxidation state, and L is 1,4-diphenyl-1,3-butadiene or 1,3-pentadiene.

Especially preferred coordination complexes corresponding to the previous formula (ID) are uniquely substituted depending on the particular end use thereof. In particular, highly useful metal complexes for use in catalyst compositions for the copolymerization of ethylene, one or more monovinyl aromatic monomers, and optionally an α-olefin, cyclicolefin or diolefin comprise the foregoing complexes (ID) wherein M is titanium, X is chloride or methyl, Z' is dimethylsilandiyl, Y is t-butylamido or phenylamido, x is 2, and l and x' are 0, or wherein M is titanium, X' is 1,3-pentadiene, Z' is dimethylsilandiyl, Y is t-butylamido or phenylamido, x and x' are 0 and l is 1.

Illustrative metal complexes that may be employed in the practice of the present invention include:

(t-butylamido)dimethyl(1H-cyclopenta[l]-phenanthreneyl)silanetitanium(II) 1,4-diphenyl-1,3-butadiene,
(t-butylamido)dimethyl(1H-cyclopenta[l]-phenanthreneyl)silanetitanium(II) 1,3-pentadiene,
(t-butylamido)dimethyl(1H-cyclopenta[l]-phenanthreneyl)silanetitanium(III) 2-(N,N-dimethylamino)benzyl,
(t-butylamido)dimethyl(1H-cyclopenta[l]-phenanthreneyl)silanetitanium(IV) dichloride,
(t-butylamido)dimethyl(1H-cyclopenta[l]-phenanthreneyl)silanetitanium(IV) dimethyl,
(t-butylamido)dimethyl(1H-cyclopenta[l]-phenanthreneyl)silanetitanium(IV) dibenzyl,
(isopropylamido)dimethyl(1H-cyclopenta[l]-phenanthreneyl)silanetitanium(II) 1,4-diphenyl-1,3-butadiene,
(isoproptylamido)dimethyl(1H-cyclopenta[l]-phenanthreneyl)silanetitanium(II) 1,3-pentadiene,
(isopropylamido)dimethyl(1H-cyclopenta[l]-phenanthreneyl)silanetitanium(III) 2-(N,N-dimethylamino)benzyl,
(isopropylamido)dimethyl(1H-cyclopenta[l]-phenanthreneyl)silanetitanium(IV) dichloride,
(isopropylamido)dimethyl(1H-cyclopenta[l]-phenanthreneyl)silanetitanium(IV) dimethyl,
(isopropylamido)dimethyl(1H-cyclopenta[l]-phenanthreneyl)silanetitanium(IV) dibenzyl,
(benzylamido)dimethyl(1H-cyclopenta[l]-phenanthreneyl)silanetitanium(II) 1,4-diphenyl-1,3-butadiene,
(benzylamido)dimethyl(1H-cyclopenta[l]-phenanthreneyl)silanetitanium(II) 1,3-pentadiene,
(benzylamido)dimethyl(1H-cyclopenta[l]-phenanthreneyl)silanetitanium(III) 2-(N,N-dimethylamino)benzyl,
(benzylamido)dimethyl(1H-cyclopenta[l]-phenanthreneyl)silanetitanium(IV) dichloride,
(benzylamido)dimethyl(1H-cyclopenta[l]-phenanthreneyl)silanetitanium(IV) dimethyl,
(benzylamido)dimethyl(1H-cyclopenta[l]-phenanthreneyl)silanetitanium(IV) dibenzyl,
(cyclohexylamido)dimethyl(1H-cyclopenta[l]-phenanthreneyl)silanetitanium(II) 1,4-diphenyl-1,3-butadiene,
(cyclohexylamido)dimethyl(1H-cyclopenta[l]-phenanthreneyl)silanetitanium(II) 1,3-pentadiene,
(cyclohexylamido)dimethyl(1H-cyclopenta[l]-phenanthreneyl)silanetitanium(III) 2-(N,N-dimethylamino)benzyl,
(cyclohexylamido)dimethyl(1H-cyclopenta[l]-phenanthreneyl)silanetitanium(IV) dichloride,
(cyclohexylamido)dimethyl(1H-cyclopenta[l]-phenanthreneyl)silanetitanium(IV) dimethyl,
(cyclohexylamido)dimethyl(1H-cyclopenta[l]-phenanthreneyl)silanetitanium(IV) dibenzyl,
cyclododecylamido)dimethyl(1H-cyclopenta[l]-phenanthreneyl)silanetitanium(II) 1,4-diphenyl-1,3-butadiene,
(cyclododecylamido)dimethyl(1H-cyclopenta[l]-phenanthreneyl)silanetitanium(II) 1,3-pentadiene,
(cyclododecylamido)dimethyl(1H-cyclopenta[l]-phenanthreneyl)silanetitanium(III) 2-(N,N-dimethylamino)benzyl,
(cyclododecylamido)dimethyl(1H-cyclopenta[l]-phenanthreneyl)silanetitanium(IV) dichloride,
(cyclododecylamido)dimethyl(1H-cyclopenta[l]-phenanthreneyl)silanetitanium(IV) dimethyl,
(cyclododecylamido)dimethyl(1H-cyclopenta[l]-phenanthreneyl)silanetitanium(IV) dibenzyl,
(t-butylamido)dimethyl(1-methyl-1H-cyclopenta[l]-phenanthreneyl)silanetitanium(II) 1,4-diphenyl-1,3-butadiene,
(t-butylamido)dimethyl(1-methyl-1H-cyclopenta[l]-phenanthreneyl)silanetitanium(II) 1,3-pentadiene,
(t-butylamido)dimethyl(1-methyl-1H-cyclopenta[l]-phenanthreneyl)silanetitanium(III) 2-(N,N-dimethylamino)benzyl,
(t-butylamido)dimethyl(1-methyl-1H-cyclopenta[l]-phenanthreneyl)silanetitanium(IV) dichloride,
(t-butylamido)dimethyl(1-methyl-1H-cyclopenta[l]-phenanthreneyl)silanetitanium(IV) dimethyl,
(t-butylamido)dimethyl(1-methyl-1H-cyclopenta[l]-phenanthreneyl)silanetitanium(IV) dibenzyl,
(isopropylamido)dimethyl(1-methyl-1H-cyclopenta[l]-phenanthreneyl)silanetitanium(II) 1,4-diphenyl-1,3-butadiene,
(isoproptylamido)dimethyl(1-methyl-1H-cyclopenta[l]-phenanthreneyl)silanetitanium(II) 1,3-pentadiene,
(isopropylamido)dimethyl(1-methyl-1H-cyclopenta[l]-phenanthreneyl)silanetitanium(III) 2-(N,N-dimethylamino)benzyl,
(isopropylamido)dimethyl(1-methyl-1H-cyclopenta[l]-phenanthreneyl)silanetitanium(IV) dichloride,
(isopropylamido)dimethyl(1-methyl-1H-cyclopenta[l]-phenanthreneyl)silanetitanium(IV) dimethyl,
(isopropylamido)dimethyl(1-methyl-1H-cyclopenta[l]-phenanthreneyl)silanetitanium(IV) dibenzyl,
(benzylamido)dimethyl(1-methyl-1H-cyclopenta[l]-phenanthreneyl)silanetitanium(II) 1,4-diphenyl-1,3-butadiene,
(benzylamido)dimethyl(1-methyl-1H-cyclopenta[l]-phenanthreneyl)silanetitanium(I) 1,3-pentadiene,
(benzylamido)dimethyl(1-methyl-1H-cyclopenta[l]-phenanthreneyl)silanetitanium(III) 2-(N,N-dimethylamino)benzyl,
(benzylamido)dimethyl(1-methyl-1H-cyclopenta[l]-phenanthreneyl)silanetitanium(IV) dichloride,
(benzylamido)dimethyl(1-methyl-1H-cyclopenta[l]-phenanthreneyl)silanetitanium(IV) dimethyl,
(benzylamido)dimethyl(1-methyl-1H-cyclopenta[l]-phenanthreneyl)silanetitanium(IV) dibenzyl,
(cyclohexylamido)dimethyl(1-methyl-1H-cyclopenta[l]-phenanthreneyl)silanetitanium(II) 1,4-diphenyl-1,3-butadiene,
(cyclohexylamido)dimethyl(1-methyl-1H-cyclopenta[l]-phenanthreneyl)silanetitanium(II) 1,3-pentadiene,
(cyclohexylamido)dimethyl(1-methyl-1H-cyclopenta[l]-phenanthreneyl)silanetitanium(II) 2-(N,N-dimethylamino)benzyl,
(cyclohexylamido)dimethyl(1-methyl-1H-cyclopenta[l]-phenanthreneyl)silanetitanium(IV) dichloride,
(cyclohexylamido)dimethyl(1-methyl-1H-cyclopenta[l]-phenanthreneyl)silanetitanium(IV) dimethyl,
(cyclohexylamido)dimethyl(1-methyl-1H-cyclopenta[l]-phenanthreneyl)silanetitanium(IV) dibenzyl,
cyclododecylamido)dimethyl(1-methyl-1H-cyclopenta[l]-phenanthreneyl)silanetitanium(II) 1,4-diphenyl-1,3-butadiene,
(cyclododecylamido)dimethyl(1-methyl-1H-cyclopenta[l]-phenanthreneyl)silanetitanium(II) 1,3-pentadiene,
(cyclododecylamido)dimethyl(1-methyl-1H-cyclopenta[l]-phenanthreneyl)silanetitanium(III) 2-(N,N-dimethylamino)benzyl,
(cyclododecylamido)dimethyl(1-methyl-1H-cyclopenta[l]-phenanthreneyl)silanetitanium(IV) dichloride,
(cyclododecylamido)dimethyl(1-methyl-1H-cyclopenta[l]-phenanthreneyl)silanetitanium(IV) dimethyl, (cyclododecylamido)dimethyl(1-methyl-1H-cyclopenta[l]-phenanthreneyl)silanetitanium(IV) dibenzyl,
(t-butylamido)dimethyl(1,3-dimethyl-1H-cyclopenta[l]-phenanthreneyl)silanetitanium(II) 1,4-diphenyl-1,3-butadiene,
(t-butylamido)dimethyl(1,3-dimethyl-1H-cyclopenta[l]-phenanthreneyl)silanetitanium(II) 1,3-pentadiene,
(t-butylamido)dimethyl(1,3-dimethyl-1H-cyclopenta[l]-phenanthreneyl)silanetitanium(III) 2-(N,N-dimethylamino)benzyl,
(t-butylamido)dimethyl(1,3-dimethyl-1H-cyclopenta[l]-phenanthreneyl)silanetitanium(IV) dichloride,
(t-butylamido)dimethyl(1,3-dimethyl-1H-cyclopenta[l]-phenanthreneyl)silanetitanium(IV) dimethyl,
(t-butylamido)dimethyl(1,3-dimethyl-1H-cyclopenta[l]-phenanthreneyl)silanetitanium(IV) dibenzyl,
(isopropylamido)dimethyl(1,3-dimethyl-1H-cyclopenta[l]-phenanthreneyl)silanetitanium (11)1,4-diphenyl-1,3-butadiene,
(isoproptylamido)dimethyl(1,3-dimethyl-1H-cyclopenta[l]-phenanthreneyl)silanetitanium(II) 1,3-pentadiene,
(isopropylamido)dimethyl(1,3-dimethyl-1H-cyclopenta[l]-phenanthreneyl)silanetitanium(III) 2-(N,N-dimethylamino)benzyl,
(isopropylamido)dimethyl(1,3-dimethyl-1H-cyclopenta[l]-phenanthreneyl)silanetitanium(IV) dichloride,
(isopropylamido)dimethyl(1,3-dimethyl-1H-cyclopenta[l]-phenanthreneyl)silanetitanium(IV) dimethyl,
(isopropylamido)dimethyl(1,3-dimethyl-1H-cyclopenta[l]-phenanthreneyl)silanetitanium(IV) dibenzyl,
-(benzylamido)dimethyl(1,3-dimethyl-1H-cyclopenta[l]-phenanthreneyl)silanetitanium(II) 1,4-diphenyl-1,3-butadiene,
(benzylamido)dimethyl(1,3-dimethyl-1H-cyclopenta[l]-phenanthreneyl)silanetitanium(II) 1,3-pentadiene,
(benzylamido)dimethyl(1,3-dimethyl-1H-cyclopenta[l]-phenanthreneyl)silanetitanium(III) 2-(N,N-dimethylamino)benzyl,
(benzylamido)dimethyl(1,3-dimethyl-1H-cyclopenta[l]-phenanthreneyl)silanetitanium(IV) dichloride,
(benzylamido)dimethyl(1,3-dimethyl-1H-cyclopenta[l]-phenanthreneyl)silanetitanium(IV) dimethyl,
(benzylamido)dimethyl(1,3-dimethyl-1H-cyclopenta[l]-phenanthreneyl)silanetitanium(IV) dibenzyl,
(cyclohexylamido)dimethyl(1,3-dimethyl-1H-cyclopenta[l]-phenanthreneyl)silanetitanium (11)1,4-diphenyl-1,3-butadiene,
(cyclohexylamido)dimethyl(1,3-dimethyl-1H-cyclopenta[l]-phenanthreneyl)silanetitanium(II) 1,3-pentadiene,
(cyclohexylamido)dimethyl(1,3-dimethyl-1H-cyclopenta[l]-phenanthreneyl)silanetitanium(III) 2-(N,N-dimethylamino)benzyl,
(cyclohexylamido)dimethyl(1,3-dimethyl-1H-cyclopenta[l]-phenanthreneyl)silanetitanium(IV) dichloride,
(cyclohexylamido)dimethyl(1,3-dimethyl-1H-cyclopenta[l]-phenanthreneyl)silanetitanium(IV) dimethyl,
(cyclohexylamido)dimethyl(1,3-dimethyl-1H-cyclopenta[l]-phenanthreneyl)silanetitanium(IV) dibenzyl,
cyclododecylamido)dimethyl(1,3-dimethyl-1H-cyclopenta[l]-phenanthreneyl)silanetitanium (11)1,4-diphenyl-1,3-butadiene,
(cyclododecylamido)dimethyl(1,3-dimethyl-1H-cyclopenta[l]-phenanthreneyl)silanetitanium(II) 1,3-pentadiene,
(cyclododecylamido)dimethyl(1,3-dimethyl-1H-cyclopenta[l]-phenanthreneyl)silanetitanium(III) 2-(N,N-dimethylamino)benzyl,
(cyclododecylamido)dimethyl(1,3-dimethyl-1H-cyclopenta[l]-phenanthreneyl)silanetitanium(IV) dichloride,
(cyclododecylamido)dimethyl(1,3-dimethyl-1H-cyclopenta[l]-phenanthreneyl)silanetitanium(IV) dimethyl, and
(cyclododecylamido)dimethyl(1,3-dimethyl-1H-cyclopenta[l]-phenanthreneyl)silanetitanium(IV) dibenzyl.

The complexes can be prepared by combining a Group 4 metal tetrahalide or tetraamide salt with the corresponding cyclopentaphenanthrenyl ring system ligand dianion in an inert diluent. Optionally a reducing agent can be employed to produce the lower oxidation state complexes, and standard ligand exchange procedures can by used to produce different ligand substituents. Processes that are suitably adapted for use herein are well known to synthetic organometallic chemists. The syntheses are preferably conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated)derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: U.S. Pat. Nos. 5,153,157, 5,064,802, 5,321,106, 5,350,723, and EP-A-520,732 (equivalent to U.S. Ser. No. 07/876,268), the teachings of which are hereby incorporated by reference.

Combinations of neutral Lewis acids, especially the combination of a trialkyl aluminum compound having from 1 to 4 carbons in each alkyl group and a halogenated tri (hydrocarbyl)boron compound having from 1 to 20 carbons in each hydrocarbyl group, especially tris (pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluorophenyl-borane:alumoxane are from 1:1:1 to 1:5:20, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*-H)_d^+(A)^{d-}$$

wherein:
L* is a neutral Lewis base;
$(L^*-H)^+$ is a conjugate Bronsted acid of L*;
$A^{d-}$ is a noncoordinating, compatible anion having a charge of d–, and
d is an integer from 1 to 3.

More preferably $A^{d-}$ corresponds to the formula: $[M'Q_4]^-$;
wherein:
M' is boron or aluminum in the +3 formal oxidation state; and
Q independently each occurrence is selected from hydride, dialkylamido, halide, hydrocarbyl, hydrocarbyloxide, halosubstituted-hydrocarbyl, halosubstituted hydrocarbyloxy, and halo-substituted silyl-hydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred embodiment, d is one, that is, the counter ion has a single negative charge and is $A^-$. Activating cocatalysts comprising boron which are particularly useful in the preparation of catalysts of this invention may be represented by the following general formula:

$$(L^*-H)^+(BQ_4)^-;$$

wherein:
L* is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Preferred Lewis base salts are ammonium salts, more preferably trialkylammonium salts containing one or more $C_{12-40}$ alkyl groups. Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:
trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
tri(sec-butyl)ammonium tetrakis(pentafluorophenyl) borate,
N,N-dimethylanilinium tetrakis(pentafluorophenyl) borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2,3,5,6-tetrafluorophenyl) borate,
N,N-dimethylanilinium tetrakis(4-(triisopropylsilyl)-2,3,5,6-tetrafluorophenyl) borate,
N,N-dimethylanilinium pentafluorophenoxytris (pentafluorophenyl) borate,
N,N-diethylanilinium tetrakis(pentafluorophenyl) borate,
N,N-dimethyl-2,4,6-trimethylanilinium tetrakis (pentafluorophenyl) borate,
dimethyloctadecylammonium tetrakis(pentafluorophenyl) borate,
methyldioctadecylammonium tetrakis(pentafluorophenyl) borate,
dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis(pentafluorophenyl) borate, and
dioctadecylammonium tetrakis(pentafluorophenyl) borate;
tri-substituted phosphonium salts such as:
triphenylphosphonium tetrakis(pentafluorophenyl) borate,
methyldioctadecylphosphonium tetrakis(pentafluorophenyl) borate, and
tri(2,6-dimethylphenyl)phosphonium tetrakis (pentafluorophenyl) borate;

di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;
di-substituted sulfonium salts such as:
di(o-tolyl)sulfonium tetrakis(pentafluorophenyl) borate, and
methylcotadecylsulfonium tetrakis(pentafluorophenyl) borate.

Preferred $(L^*-H)^+$ cations are methyldioctadecylammonium and dimethyloctadecylammonium.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:

$Ox^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted ferrocenium, $Ag^+$, or $Pb^{+2}$. Preferred embodiments of Ad are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

$$©^+A^-$$

wherein:

$©^+$ is a $C_{1-20}$ carbenium ion; and $A^-$ is as previously defined. A preferred carbenium ion is the trityl cation, that is triphenylmethylium.

A further suitable ion forming, activating cocatalyst comprises a compound which is a salt of a silylium ion and a noncoordinating, compatible anion represented by the formula:

$$(R^6{}_3Si)^+A^-$$

wherein:

$R^6$ is $C_{1-10}$ hydrocarbyl, and $A^-$ is as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in J. Chem Soc. Chem. Comm., 1993, 383–384, as well as Lambert, J. B., et al., Organometallics, 1994, 13, 2430–2443. The use of the above silylium salts as activating cocatalysts for addition polymerization catalysts is disclosed in U.S. Pat. No. 5,625,087, the teachings of which are herein incorporated by reference.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, A-. Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium-cations.

During activation of the complexes of the present invention by bulk electrolysis the cation of the supporting electrolyte passes to the counter electrode and A- migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra (n-butylammonium)tetrakis(pentafluorophenyl) borate. The foregoing technique has been previously disclosed in U.S. Pat. No. 5,372,682, the teachings of which are hereby incorporated by reference.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any of the foregoing methods, may be used to polymerize ethylenically and/or acetylenically unsaturated monomers having from 2 to 100,000 carbon atoms either alone or in combination. The monomers for use herein include aliphatic and aromatic compounds containing vinylic unsaturation, as well as cyclic unsaturated compounds such as cyclobutene, cyclopentene, and norbornene, including norbornene substituted in the 5 and 6 position with $C_{1-20}$ hydrocarbyl groups, and diolefins. Also included are mixtures of such monomers, especially mixtures of $C_{2-8}$ olefins with $C_{4-40}$ diolefin compounds. Examples of the latter compounds include ethylidenenorbornene, 1,4-hexadiene, and norbornadiene. Long chain vinyl terminated monomers may be formed during the polymerization process, for example by the phenomenon of β-hydride elimination of a proton from a growing polymer chain. This process results in incorporation of such extremely long chains of preformed polymer into the resulting polymer, i. e. long chain branching. The catalysts and processes herein are especially suited for use in preparation of ethylene/propylene, ethylene/1-butene, ethylene/1-hexene, ethylene/styrene, and ethylene/1-octene copolymers as well as terpolymers of ethylene, propylene and a nonconjugated diene, referred to as EPDM polymers, terpolymers of ethylene, propylene and styrene, referred to as EPS polymers, or terpolymers of ethylene, styrene and a nonconjugated diene, referred to as ESDM polymers.

Vinylaromatic monomers for use herein include $C_{8-20}$ aryl substituted ethylene compounds having the formula:

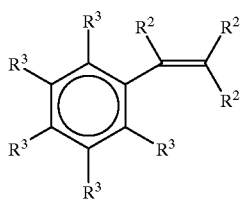

wherein:

$R^2$ independently each occurrence is hydrogen or $C_{1-4}$ alkyl, and $R^3$ independently each occurrence is $R^2$ or halo.

Preferred monomers include the $C_{2-20}$ olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, Cl-4 alkyl substituted styrene, tetrafluoroethylene, norbornene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene.

More preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}:1$ to $10^{-1}:1$, more preferably from $10^{-9}:1$ to $10^{-5}:1$.

Suitable solvents use for solution polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993, the teachings of which are hereby incorporated by reference herein.

Utilizing the present catalysts, interpolymers of ethylene, one or more vinylaromatic monomers and optionally an α-olefin or a diolefin having densities from 0.85 g/cm³ to 1.1 g/cm³, melt flow rates from 0.01 to 20.0 dg/min, and incorporating large amounts of vinylaromatic monomer in a pseudo-random manner are readily attained in a highly efficient process. Pseudo-random incorporation of vinylaromatic monomers is a well known phenomena in which the monomer is essentially randomly incorporated into the polymer, excepting that two such vinylaromatic monomers having the same orientation may not succeed one another in the polymer chain. The procedure has been previously disclosed in U.S. Pat. No. 5,703,187, the teachings of which are herein incorporated by reference.

The catalysts of the present invention are also particularly advantageous for the production of ethylene homopolymers, ethylene/α-olefin copolymers, and interpolymers of ethylene a diene and optionally a $C_{3-20}$ α-olefin having high levels of long chain branching and comonomer incorporation. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent in which polymerization will be carried out by solution polymerization procedures. The catalyst composition may also be prepared and employed as a heterogeneous catalyst by adsorbing the requisite components on an inert inorganic or organic particulated solid. Examples of such solids include, silica, silica gel, alumina, trialkylaluminum compounds, and organic or inorganic polymeric materials, especially polyolefins. In an preferred embodiment, a heterogeneous catalyst is prepared by co-precipitating the metal complex, an inert, inorganic compound and an activator, especially an ammonium salt of a hydroxyaryl (trispentafluorophenyl)borate, such as an ammonium salt of (4-hydroxy-3,5-ditertiarybutylphenyl) (trispentafluorophenylborate. A preferred inert, inorganic compound for use in this embodiment is a tri ($C_{1-4}$ alkyl) aluminum compound.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably at least a major part of the diluent comprises the α-olefin monomer or monomers to be polymerized.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

The polymerization may be carried out as a batchwise or a continuous polymerization process A continuous process is preferred, in which event catalyst, ethylene, comonomer, and optionally solvent are continuously supplied to the reaction zone and polymer product continuously removed therefrom.

Without limiting in any way the scope of the invention, one means for carrying out such a polymerization process is as follows: In a stirred-tank reactor, the monomers to be polymerized are introduced continuously together with solvent and an optional chain transfer agent. The reactor contains a liquid phase composed substantially of monomers together with any solvent or additional diluent and dissolved polymer. If desired, a small amount of a "H"-branch inducing diene such as norbornadiene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mentioned chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours. By using a catalyst that incorporates large amounts of hindered monovinyl monomer, such as a vinylaromatic monomer, hindered monovinyl homopolymer formed from residual quantities of the monomer are substantially reduced.

As previously mentioned, the catalysts of the invention are capable of producing novel ES polymers. Particularly when used in a continuous polymerization process, especially a continuous solution polymerization process, the resulting ES polymer has been found to contain highly uniform vinylaromatic monomer incorporation. Such uniform ES polymers are characterized by a unique $^{13}$C NMR signature. In particular, such polymers are characterized by a cluster index, $CI_{ES}$, which relates a ratio of two peaks in the $^{13}$C NMR spectrum, $NMR_F/NMR_E$, wherein $NMR_F$ is the integrated area of the peak associated only with vinylaromatic monomer/ethylene/vinylaromatic monomer (SES) triads (commonly appearing at approximately 25 to 26.9 ppm) and $NMR_E$ is the integrated area of the peak associated only with triads containing a single incorporated vinylaromatic monomer (commonly appearing at approximately 27 to 29 ppm). It should be emphasized that in both types of polymers the vinylaromatic monomer is incorporated in a pseudo random manner, that is, successive or adjacent head to tail insertion of a vinyl aromatic monomer in the polymer chain is still prohibited. Such pseudo random nature characteristically produces a $^1$H NMR spectrum of the polymer which lacks any appreciable peaks between the two peaks located at approximately 37 and 46 ppm respectively. However, in uniform ES polymers, lack of clustering of the incorporated vinylaromatic monomer into alternating monomer sequences can be identified by comparing the area of the $NMR_E$ peaks relative to $NMR_F$ peaks as a function of monomer composition in the polymer.

This cluster index, $CI_{ES}$, can be expressed mathematically through use of the following formula:

$$CI_{ES} = \left[\frac{NMR_F}{NMR_E}\right]\left[\frac{(4F_1 - 2)}{(1 - F_1)}\right]$$

where $F_1$ is the mole fraction of ethylene in the polymer. The uniform pseudo-random ES polymers of the invention are characterized by $CI_{ES}$ values less than 1.0 at polymer compositions of less than 50 mole percent polymerized vinylaromatic monomer, preferably $CI_{ES}$ values less than 0.95 at compositions of less than 47 mole percent polymerized vinylaromatic monomer.

The process of the present invention can be employed to advantage in the gas phase copolymerization of olefins. Gas phase processes for the polymerization of olefins, especially the homopolymerization and copolymerization of ethylene and propylene, and the copolymerization of ethylene with higher α-olefins such as, for example, 1-butene, 1-hexene, 4-methyl-1-pentene are well known in the art. In such processes, cooling of the reactor may be provided by the use of recycle gas, which is fed as a volatile liquid to the bed to provide an evaporative cooling effect. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid (or can be condensed to provide such a liquid) this can be fed to the bed to provide an evaporative cooling effect. Examples of olefin monomers which can be employed in this manner are olefins containing three to eight, preferably three to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream. This type of process is described, for example in EP 89691; U.S. Pat. No. 4,543,399; WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032, the teachings of which is hereby incorporated by reference.

The polymerization reaction occurring in the gas fluidized bed is catalyzed by the continuous or semi-continuous addition of catalyst. Such catalyst can be supported on an inorganic or organic support material as described above.

The polymer is produced directly in the fluidized bed by catalyzed copolymerization of the monomer and one or more comonomers on the fluidized particles of catalyst, supported catalyst or prepolymer within the bed. Start-up of the polymerization reaction is achieved using a bed of preformed polymer particles, which are preferably similar to the target polyolefin, and conditioning the bed according to techniques that are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a larger cross-sectional area than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization. The produced polymer is discharged continuously or discontinuously from the fluidized bed as desired.

The gas phase processes suitable for the practice of this invention are preferably continuous processes which provide for the continuous supply of reactants to the reaction zone of the reactor and the removal of products from the reaction zone of the reactor, thereby providing a steady-state environment on the macro scale in the reaction zone of the reactor.

Typically, the fluidized bed of the gas phase process is operated at temperatures greater than 50° C., preferably from 60° C. to 110° C., more preferably from 70° C. to 110° C.

Typically the molar ratio of comonomer to monomer used in the polymerization depends upon the desired density for the composition being produced and is 0.5 or less. Desirably, when producing materials with a density range of from 0.91 to 0.93 the comonomer to monomer ratio is less than 0.2, preferably less than 0.05, even more preferably less than 0.02, and may even be less than 0.01. Typically, the ratio of hydrogen to monomer is less than 0.5, preferably less than 0.2, more preferably less than 0.05, even more preferably less than 0.02 and may even be less than 0.01.

The above-described ranges of process variables are appropriate for the gas phase process of this invention and may be suitable for other processes adaptable to the practice of this invention.

A number of patents and patent applications describe gas phase processes which are adaptable for use in the process of this invention, particularly, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,541,270 and EP applications 659,773; 692,500; and PCT Applications WO 94/29032, WO 94/25497, WO 94/25495, WO 94/28032; WO 95/13305; WO 94/26793; and WO 95/07942 the teachings of all of which are hereby incorporated herein by reference.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. All syntheses were performed under dry nitrogen atmosphere using a combination of glove box and high vacuum techniques. The term "overnight" refers to a period of time from 14 to 20 hours. The term "room temperature" refers to a temperature from 20 to 25° C.

Example 1

Preparation of lithium 1H-cyclopenta[l]phenanthrene-2-yl

To a 250 ml round bottom flask containing 1.42 g (0.00657 mole) of 1H-cyclopenta[l]phenanthrene and 120 ml of benzene was added dropwise, 4.2 ml of a 1.60 M solution of n-BuLi in mixed hexanes. The solution was allowed to stir overnight. The lithium salt was isolated by filtration, washing twice with 25 ml benzene and drying under vacuum. Isolated yield was 1.426 g (97.7 percent).

Preparation of (1H-cyclopenta[l]phenanthrene-1-yl)dimethylchlorosilane

To a 500 ml round bottom flask containing 4.16 g (0.0322 mole) of dimethyldichlorosilane ($Me_2SiCl_2$) and 250 ml of tetrahydrofuran (THF) was added dropwise a solution of 1.45 g (0.0064 mole) of lithium 1H-cyclopenta[l]phenanthrene-2-yl in THF. The solution was stirred for approximately 16 hours, after which the solvent was removed under reduced pressure, leaving an oily solid which was extracted with toluene, filtered through diatomaceous earth filter aid (Celite™), washed twice with toluene and dried under reduced pressure. Isolated yield was 1.98 g (99.5 percent). $^1H$ NMR analysis indicated the predominant isomer was substituted at the 1 position.

Preparation of (1H-cyclopenta[l]phenanthrene-2-yl)dimethyl(t-butylamino)silane

To a 500 ml round bottom flask containing 1.98 g (0.0064 mole) of (1H-cyclopenta[l]phenanthrene-2-yl)dimethylchlorosilane and 250 ml of hexane was added 2.00 ml (0.0160 mole) of t-butylamine. The reaction mixture was allowed to stir for several days, then filtered using diatomaceous earth filter aid (Celite™), washed twice with hexane. The product was isolated by removing residual solvent under reduced pressure. The isolated yield was 1.98 g (88.9 percent). $^1H$ NMR analysis indicated the predominant isomer was substituted at the 2 position due to migration of the silane substituent.

Preparation of dilithio (1H-cyclopenta[l]phenanthrene-2-yl)dimethyl(t-butylamido)silane To a 250 ml round bottom flask containing 1.03 g (0.0030 mole) of (1H-cyclopenta[l]phenanthrene-2-yl)dimethyl(t-butylamino)silane) and 120 ml of benzene was added dropwise 3.90 ml of a solution of 1.6 M n-BuLi in mixed hexanes. The reaction mixture was stirred for approximately 16 hours. The product was isolated by filtration, washed twice with benzene and dried under reduced pressure. Isolated yield was 1.08 g (100 percent).

Preparation of (1H-cyclopenta[l]phenanthrene-2-yl)dimethyl(t-butylamido)silanetitanium dichloride To a 250 ml round bottom flask containing 1.17 g (0.0030 mole) of $TiCl_3.3THF$ and 120 ml of THF was added at a fast drip rate 50 ml of a THF solution of 1.08 g of dilithio (1H-cyclopenta[l]phenanthrene-2-yl)dimethyl(t-butylamido)silane. The mixture was stirred at 20–25° C. for 1.5 h at which time 0.55 gm (0.002 mole) of solid $PbCl_2$ was added. After stirring for an additional 1.5 h the THF was removed under vacuum and the reside was extracted with toluene, filtered and dried under reduced pressure to give an orange solid. Yield was 1.31 g (93.5 percent).

Example 2

Preparation of (1H-cyclopenta[l]phenanthrene-2-yl)dimethyl(t-butylamido)silanetitanium dimethyl To a 100 ml round bottom flask containing 0.480 g (0.00104 mole) of (1H-cyclopenta[l]phenanthrene-2-yl) dimethyl(t-butylamido)silanetitanium dichloride and 50 ml of diethylether was added dropwise 0.75 ml of a 3.0 M solution of MeMgBr in diethylether. The reaction mixture was allowed to stir for 0.5 h. The volatiles were removed under reduced pressure and the residue was extracted with hexane and then filtered. The desired product was isolated by removing the solvent under reduced pressure to give 0.196 g (44.8 percent yield) of a yellow solid.

Example 3

Preparation of (1H-cyclopenta[l]phenanthrene-2-yl)dimethyl(t-butylamido)silanetitanium 1,4-diphenylbutadiene To a slurry of (1H-cyclopenta[l]phenanthrene-2-yl)dimethyl(t-butylamido)silanetitanium dichloride (3.48 g, 0.0075mole) (produced by scaling up Example 1) and 1.551 gm (0.0075 mole) of 1,4-diphenyllbutadiene in 80 ml of toluene at 70° C. was add 9.9 ml of a 1.6 M solution of n-BuLi (0.0150 mole). The solution immediately darkened. The temperature was increased to bring the mixture to reflux and the mixture was maintained at that temperature for 2 hrs. The mixture was cooled to −20 ° C. and the volatiles were removed under reduced pressure. The residue was slurried in 60 ml of mixed hexanes at 20–25° C. for approximately 16 hours. The mixture was cooled to −25° C. for 1 h. The solids were collected on a glass frit by vacuum filtration and dried under reduced pressure. The dried solid was placed in a glass fiber thimble and solid extracted continuously with hexanes using a soxhlet extractor. After 6 h a crystalline solid was observed in the boiling pot. The mixture was cooled to −20° C., isolated by filtration from the cold mixture and dried under reduced pressure to give 1.62 g of a dark crystalline solid. The filtrate was discarded. The solids in the extractor were stirred and the extraction continued with an additional quantity of mixed hexanes to give an additional 0.46 gm of the desired product as a dark crystalline solid.

A sample of the product was examined by X-ray diffraction, $^1H$ NMR spectroscopy, $^{13}C$ NMR spectroscopy, elemental analysis and X-ray diffraction. The ORTEP generated from the single crystal X-ray analysis is contained in FIG. 1. Powder X-ray diffraction analysis confirmed that the sample was representative of the product.

Example 4

(1-methyl-1H-cyclopenta[l]phenanthrene-2-yl)dimethyl(t-butylamido)silanetitanium dichloride Preparation of lithium 3-methyl-1H-cyclopenta[l]phenanthrene-2-yl To a 250 ml round bottom flask containing 1.26 g (0.00547 mole) of 3-methyl-1H-cyclopenta[l]phenanthrene and 120 ml of benzene was added dropwise, 3.60 ml of a 1.60 M solution of n-BuLi in mixed hexanes. The solution was allowed to stir overnight. The lithium salt was isolated by filtration, washing twice with 25 ml benzene and drying under vacuum. Isolated yield was 1.250 g (96.9 percent).

Preparation of (1-methyl-1H-cyclopenta[l]phenanthrene-2-yl)dimethylchlorosilane

To a 500 ml round bottom flask containing 1.71 g (0.01323 mole) of dimethyidichlorosilane ($Me_2SiCl_2$) and 250 ml of tetrahydrofuran (THF) was added dropwise a solution of 1.25 g (0.00529 mole) of lithium 3-methyl-1H-cyclopenta[l]phenanthrene-2-yl in 60 ml THF. The solution was stirred overnight, after which the solvent was removed under reduced pressure, leaving a solid which was extracted with toluene, filtered through diatomaceous earth filter aid (Celite™), washed twice with toluene and dried under reduced pressure. Isolated yield was 1.699 g (97.7 percent). $^1H$ NMR analysis indicated the predominant isomer was substituted at the 1 position.

Preparation of (1-methyl-1H-cyclopenta[l]phenanthrene-2-yl)dimethyl(t-butylamino)silane To a 500 ml round bottom flask containing 1.699 g (0.00526 mole) of (1-methyl-1H-cyclopenta[l]phenanthrene-2-yl)dimethylchlorosilane and 100 ml of hexane and 150 ml toluene was added 0.975 g (0.0132 mole) of t-butylamine. The reaction mixture was allowed to stir for several days, then filtered using diatomaceous earth filter aid (Celite™), washed twice with hexane. The product was isolated by removing residual solvent under reduced pressure. The isolated yield was 1.785 g (94.6 percent). 1H NMR analysis indicated the predominant isomer was substituted at the 2 position.

Preparation of dilithio (1-methyl-1H-cyclopenta[l]phenanthrene-2-yl)dimethyl(t-butylamido)silane To a 500 ml round bottom flask containing 1.7785 g (0.00498 mole) of (1-methyl-1H-cyclopenta[l]phenanthrene-2-yl)dimethyl(t-butylamino)silane) and 120 ml of hexane was added dropwise 6.50 ml of a solution of 1.6 M n-BuLi in mixed hexanes. The reaction mixture was stirred overnight. The product was isolated by filtration, washed twice with hexane and dried under reduced pressure. Isolated yield was 1.544 g (83.7 percent).

Preparation of (1-methyl-1H-cyclopenta[l]phenanthrene-2-yl)dimethyl(t-butylamido)silanetitanium dichloride To a 250 ml round bottom flask containing 1.540 g (0.00417 mole) of $TiCl_3.3THF$ and 130 ml of THF was added at a fast drip rate 50 ml of a THF solution of 1.544 g of dilithio (1-methyl-1H-cyclopenta[l]phenanthrene-2-yl)dimethyl(t-butylamido)silane. The mixture was stirred at 20–25° C. for 1.5 h at which time 0.64 gm (0.0023 mole) of solid $PbCl_2$ was added. After stirring for an additional 1.25 h the THF was removed under vacuum and the reside was extracted with toluene, filtered and dried under reduced pressure to give an orange/brown solid. Yield was 0.84 g (42.3 percent).

Example 5
Preparation of (1-methyl-1H-cyclopenta[l]phenanthrene-2-yl)dimethyl(t-butylamido)silanetitanium dimethyl To a 100 ml round bottom flask containing 0.790 g (0.00147 mole) of (1-methyl-1H-cyclopenta[l]phenanthrene-2-yl)dimethyl(t-butylamido)silanetitanium dichloride and 50 ml of diethylether was added dropwise 1.03 ml of a 3.0 M solution of MeMgBr in diethylether. The reaction mixture was allowed to stir for 2.0 h. The volatiles were removed under reduced pressure and the residue was extracted with hexane and then filtered. The desired product was isolated by removing the solvent under reduced pressure to give 0.480 g (75.0 percent yield) of a dirty yellow solid.

Example 6
(1,3-dimethyl-1H-cyclopenta[l]phenanthrene-2-yl)dimethyl (t-butylamido)silanetitanium dichloride
Preparation of lithium 1,3-dimethyl-1H -cyclopenta[l]phenanthrene-2-yl To a 500 ml round bottom flask containing 1.90 g (0.00781 mole) of 1,3-dimethyl-1H-cyclopenta[l]phenanthrene and 2250 ml of benzene/toluene was added dropwise, 5.36 ml of a 1.60 M solution of n-BuLi in mixed hexanes. The solution was allowed to stir overnight. The lithium salt was isolated by filtration, washing twice with 25 ml benzene and drying under vacuum. Isolated yield was 1.898 g (97.5 percent).

Preparation of (1,3-dimethyl-1H-cyclopenta[l]phenanthrene-2-yl)dimethylchlorosilane To a 500 ml round bottom flask containing 4.92 g (0.0381 mole) of dimethyldichlorosilane ($Me_2SiCl_2$) and 250 ml of tetrahydrofuran (THF) was added via a slow dropwise addition of a solution of 1.898 g (0.00761 mole) of lithium 1,3-dimethyl-1H-cyclopenta[l]phenanthrene-2-yl in 60 ml THF. The solution was stirred overnight, after which the solvent was removed under reduced pressure, leaving a solid which was extracted with toluene, filtered through diatomaceous earth filter aid (Celite™), washed twice with toluene and dried under reduced pressure. Isolated yield was 2.420 g (92.4 percent). 1H NMR analysis indicated the predominant isomer was substituted at the 1 position.

Preparation of (1,3-dimethyl-1H -cyclopenta[l]phenanthrene-2-yl)dimethyl(t-butylamino)silane To a 500 ml round bottom flask containing 2.420 g (0.00718 mole) of (1,3-dimethyl-1H-cyclopenta[l]phenanthrene-2-yl)dimethylchlorosilane and 250 ml of methylene chloride was added 1.331 g (0.0180 mole) of t-butylamine. The reaction mixture was allowed to stir for several days, then filtered using diatomaceous earth filter aid (Celite™), washed twice with hexane. The product was isolated by removing residual solvent under reduced pressure. The isolated yield was 2.120 g (79.0 percent). $^1H$ NMR analysis indicated the predominant isomer was substituted at the 2 position.

Preparation of dilithio (1,3-dimethyl-1H-cyclopenta[l]phenanthrene-2-yl)dimethyl(t-butylamido)silane To a 500 ml round bottom flask containing 2.120 g (0.00567 mole) of (1,3-dimethyl-1H-cyclopenta[l]phenanthrene-2-yl)dimethyl(t-butylamino)silane) and 250 ml of hexane was added dropwise 7.8 ml of a solution of 1.6 M n-BuLi in mixed hexanes. The reaction mixture was stirred overnight. The product was isolated by filtration, washed twice with hexane and dried under reduced pressure. Isolated yield was 1.847 g (84.7 percent).

Preparation of (1,3-dimethyl-1H-cyclopenta[l]phenanthrene-2-yl)dimethyl(t-butylamido)silanetitanium dichloride To a 500 ml round bottom flask containing 1.771 g (0.00479 mole) of $TiCl_3.03THF$ and 250 ml of THF was added at a fast drip rate 75 ml of a THF solution of 1.847 g of dilithio (1,3-dimethyl-1H-cyclopenta[l]phenanthrene-2-yl)dimethyl(t-butylamido)silane. The mixture was stirred at 20–25° C. for 1.5 h at which time 0.733 gm (0.0026 mole) of solid $PbCl_2$ was added. After stirring for an additional 1.5 h the THF was removed under vacuum and the reside was extracted with hot toluene, cooled filtered and dried under reduced pressure to give an orange solid. Yield was 0.80 g (34.5 percent).

Example 7
Preparation of (1,3-dimethyl-1H-cyclopenta[l]phenanthrene-2-yl)dimethyl(t-butylamido)silanetitanium dimethyl To a 100 ml round bottom flask containing 0.320 g (0.00065 mole) of (1,3-dimethyl-1H-cyclopenta[l]phenanthrene-2-yl)dimethyl(t-butylamido)silanetitanium dichloride and 50 ml of diethylether was added dropwise 0.446 ml of a 3.0 M solution of MeMgBr in diethylether. The reaction mixture was allowed to stir for 2.0 h. The volatiles were removed under reduced pressure and the residue was extracted with hexane and then filtered. The desired product was isolated by removing the solvent under reduced pressure to give 0.239 g (81.6 percent yield) of a deep yellow solid.

Polymerization Examples
Ethylene/styrene copolymerization

The polymerization conditions were as follows: A two-liter Parr reactor was charged with approximately 360 g of Isopar-E™ mixed alkanes solvent (available from Exxon Chemicals Inc.) and 460 g of styrene comonomer. Hydrogen was added as a molecular weight control agent by differential pressure expansion from a 75 mL addition tank at 50 psig (345 kPa). The reactor was heated to 90° C. and saturated with ethylene at 200 psig (1.4 MPa). The appropriate amount of catalyst and cocatalyst (trispentafluorophenylborane) as 0.005M solutions in toluene (approximately 3 μmole) were premixed in a glovebox to give a 1:1 molar ratio of catalyst and cocatalyst, and transferred to a catalyst addition tank and injected into the reactor. The polymerization conditions were maintained for 30 minutes with ethylene on demand. The resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos 168). Polymers formed are dried in a programmed vacuum oven with a maximum temperature of 130° C. and a 20 hours heating cycle. Results are shown in Table 1.

TABLE 1

| Run | complex | Yield (g) | Efficiency[1] | styrene[2] |
|---|---|---|---|---|
| 1 | Example 2 | 133.7 | 0.93 | 30.9 |
| 2 | Example 3 | 202.6 | 1.06 | 30.5 |
| 3 | Example 5 | 85.3 | 0.26 | 29.4 |
| 4 | Example 7 | 112.6 | 0.39 | 31.6 |
| compare A | TMCTP* | 63 | 0.22 | 13 |

[1]Kg polymer/g titanium
[2]mole percent styrene
*(t-butylamido)dimethyl($\eta^5$-tetramethylcyclopentadienyl)titanium 1,3-pentadiene Continuous Polymerizations and Composition Index Calculation Reactor A continuous loop reactor operating under isothermal polymerization conditions was prepared for use. The reactor loop was composed of two ½" (1.27cm) Koch SMX static mixers, a custom, 1200 mL/min, magnetically coupled, Micropump® gear pump and assorted ½" (1.27cm) Swagelok® tube fittings. The loop was equipped with two inlets, one for metered flows of purified ethylene, hydrogen, toluene and styrene or mixtures of styrene and toluene, the other for the active catalyst system. A pressure transducer on the feed inlet and a dual thermocouple in the loop provided inputs for computerized control of reactor pressure and temperature via electrical heating tapes on the static mixers and an electrically operated control valve on the reactor outlet. An in-line viscometer (available from Cambridge Applied Scientifics Corporation) was used to monitor the outlet flow.

Process Conditions

Styrene (with 12 ppm t-butylcatechol) and 2,4-dinitro-p-cresol (20 ppm) was placed in a 20 lb. propane cylinder, sparged with helium and then pumped through a 1.5"×20" (3.8×50.8 cm) column packed with activated A-204 alumina (available from Kaiser Aluminum Co.). Toluene solvent was stored in a 20 gallon cylinder, sparged with helium and pumped through two 2"×30" (5.1×76.2 cm) columns, one packed with activated A-2 alumina and 3 Å molecular sieves, the other with activated oxygen reactant (available from Engelhard Corporation under the trade designation Q-5®, Cu-0226 S).

The metal complex, (1H-cyclopenta[1]phenanthrene-2-yl) dimethyl(t-butylamido)silanetitanium 1,4-diphenylbutadiene, was used as a 1.00×10$^{-3}$ M solution in toluene. Tris(pentafluorophenyl)borane cocatalyst (FAB) was prepared as a 2.00×10$^{-3}$ M solution in toluene and was delivered to the reactor in a 1:1 (by volume) mixture with the metal complex solution.

The reaction was monitored in-situ by a fiber-optic FTNIR spectrometer calibrated for various mixtures of ethylene and styrene in toluene over a broad temperature range. The measured ethylene and styrene concentrations were used to determine conversions based on the known feed rates. The measured conversions were in turn used as the input for the controller which varied the catalyst feed rate in order to maintain a conversion set point.

The polymer solution was quenched upon exiting the reactor with a toluene solution consisting of isopropyl alcohol (15 ml/l), and a hindered phenol antioxidant (0.02 g/ml). The cooled polymer solution was placed in a vacuum oven in which the temperature was slowly raised from 40° C. to 130° C. overnight. The polymer was cooled to below 50° C. before removing it from the vacuum oven the next day.

A comparative ES copolymer was also prepared under similar continuous solution polymerization conditions but using the metal complex (t-butylamido)dimethyl($\eta^5$-tetramethylcyclopentadienyl)silanetitanium dimethyl. A 50 percent by weight highly pure solution of styrene in toluene was continuously pumped into the reactor. Hydrogen was also added to the reactor. The operation parameters for the polymerization experiments are given in Table 2.

TABLE 2

| run | Toluene (mL/min) | Styrene (mL/min) | Ethylene (g/min) | Catalyst (mL/min) | Temp. (° C.) | H$_2$ (mg/min) |
|---|---|---|---|---|---|---|
| 5 | 11.05 | 2.00 | 0.600 | 0.235 | 100.0 | — |
| compare B | * | * | 0.636 | 0.200 | 60.0 | 0.4 |

Figure 2:
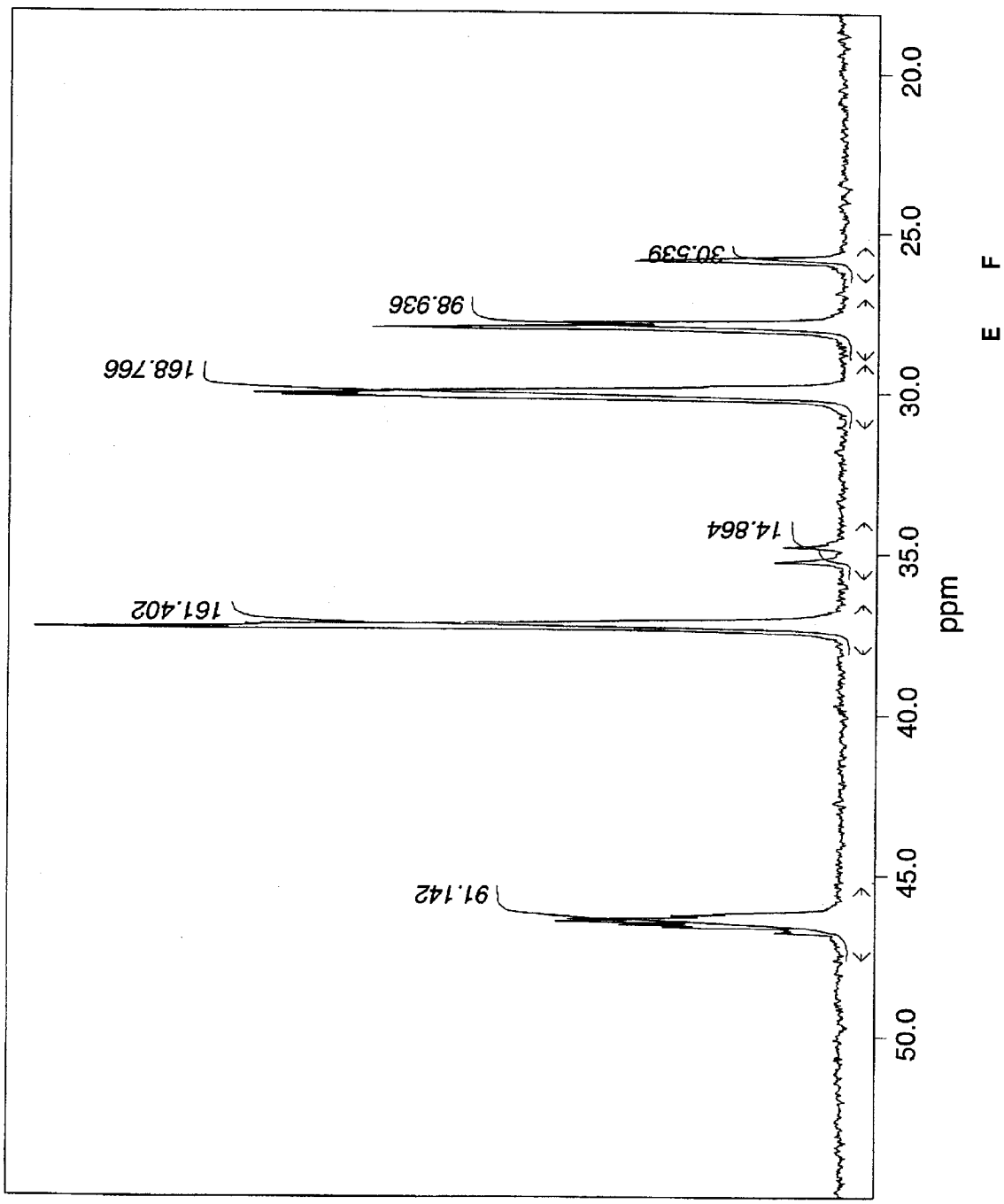
FIG. 2 is the $^1$H NMR spectrum of the ES copolymer of run 5.

*The 50 percent by weight styrene solution in toluene was added at a rate of 12.1 ml/min The resulting ES copolymers were pseudo random (characterized by a lack of any appreciable peaks in the $^1$H NMR spectrum of the polymer between the two peaks located at approximately 37 and 46 ppm respectively). The polymerized styrene content of the ES copolymer of run 5 and comparison B were 31.3 and 31.6 mole percent respectively. FIG. 2 contains the $^1$H NMR spectrum of the polymer formed in run 5. Comparison of the $^1$H NMR spectrum for comparison B polymer indicates a difference in the ratios of the two peaks labled E and F. Using the respective integrated peak areas of the respective $^1$H NMR spectra, the respective cluster indices (CI$_{ES}$) determined according to the following formula can be compared:.

$$CI_{ES} = \left[\frac{NMR_F}{NMR_E}\right]\left[\frac{(4F_1 - 2)}{(1 - F_1)}\right].$$

The calculations are as follows:

$$\text{Run 5:} \quad CI_{ES} = \left[\frac{30.539}{98.936}\right]\left[\frac{(4(0.687) - 2)}{(1 - 0.687)}\right] = 0.74$$

$$\text{Compare B:} \quad CI_{ES} = \left[\frac{42.6}{61.2}\right]\left[\frac{(4(0.684) - 2)}{(1 - 0.684)}\right] = 1.62$$

It may be seen that the copolymer of the invention has a CI$_{ES}$ of less than 1.0, whereas the comparative ES copolymer has a CI$_{ES}$ of greater than 1.0, thereby indicating less uniform incorporation of monovinylaromatic monomer.

What is claimed is:

1. A metal complex corresponding to the formula:

$$CpZMX_xL_lX'_{x'},\quad (1A);$$

where Cp is a cyclopentaphenanthrenyl ring system ligand optionally substituted with one or more ligand groups selected from hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylenephosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl ligand groups, said ligand group having up to 40 atoms not counting hydrogen atoms, and optionally two or more of the foregoing ligand groups may together form a divalent derivative, and further optionally one or more carbons of the cyclopentaphenanthrenyl ring system may be replaced by a nitrogen or phosphorus atom;

M is titanium, zirconium or hafnium in the +2, +3 or +4 formal oxidation state;

Z is either a cyclic or noncyclic ligand group containing delocalized π-eletrons, including a second cyclopentaphenanthrenyl ring system group as herein previously disclosed for Cp, said Z being bonded to M by means of delocalized π-eletrons and optionally covalently bonded to Cp through a divalent bridging group, or Z is a divalent moiety lacking in delocalized π-electrons that is covalently bonded to Cp and M, or such a moiety comprising one σ-bond by which it is bonded to Cp, and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms other than hydrogen;

L each occurrence is independently a neutral ligating compound having up to 20 atoms;

X' is a divalent anionic ligand group having up to 60 atoms;

x is 0, 1, 2, or 3;

l is a number from 0 to 2, and x' is 0 or 1.

2. A metal complex according to claim 1 corresponding to the formula:

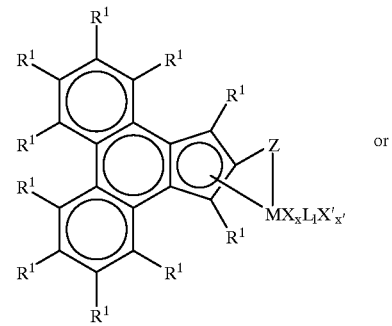

(IB)

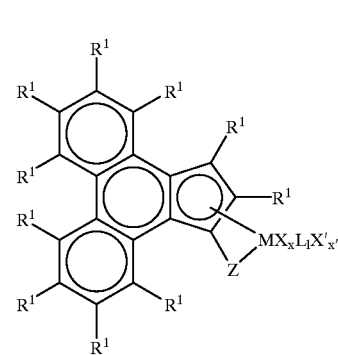

(IC)

where M is titanium, zirconium or hafnium in the +2, +3 or +4 formal oxidation state;

$R^1$ independently each occurrence is hydrogen, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said $R^1$ group having up to 40 atoms not counting hydrogen atoms, and optionally two or more of the foregoing adjacent $R^1$ groups may together form a divalent derivative thereby forming a saturated or unsaturated fused ring, and further optionally one or more of the carbons of any of the rings may be replaced by a nitrogen or sulfur atom;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L each occurrence is independently a neutral ligating compound having up to 20 atoms;

X' is a divalent anionic ligand group having up to 60 atoms;

29 x is 0, 1, 2, or 3;
l is a number from 0 to 2, and
x' is 0 or 1.

3. A complex according to claim 2 corresponding to the formula:

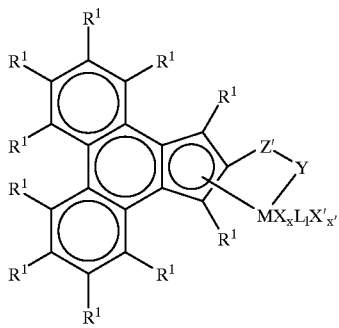

(ID)

wherein:
M is titanium;
$R^1$ each occurrence is hydrogen or a hydrocarbyl, amino or amino-substituted hydrocarbyl group of up to 20 atoms other than hydrogen;
Y is —O—, —S—, —NR$^5$—, —PR$^5$—; —NR$^5_2$, or —PR$^5_2$;
Z' is SiR$^5_2$, CR$^5_2$, SiR$^5_2$SiR$^5_2$, CR$^5_2$CR$^5_2$, CR$^5$=CR$^5$, CR$^5_2$SiR$^5_2$, BR$^5$, or GeR$^5_2$;
$R^5$ each occurrence is independently hydrogen, or a member selected from hydrocarbyl, hydrocarbyloxy, silyl, halogenated alkyl, halogenated aryl, and combinations thereof, said $R^5$ having up to 20 non-hydrogen atoms, and optionally, two $R^5$ groups from Z' (when $R^5$ is not hydrogen), or an $R^5$ group from Z' and an $R^5$ group from Y form a ring system;
X, L, and X' are as previously defined;
x is 0, 1 or 2;
l is 0 or 1; and
x' is 0 or 1;
with the proviso that:
when x is 2, x' is zero, M is in the +4 formal oxidation state (or M is in the +3 formal oxidation state if Y is —NR$^5_2$ or —PR$^5_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen,
when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms,
when x is 1, and x' is 0, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and
when x and x' are both 0, l is 1, M is in the +2 formal oxidation state, and L is a neutral, conjugated or

30 nonconjugated diene, optionally substituted with one or more hydrocarbyl groups, said L having up to 40 carbon atoms and being bound to M by means of delocalized π-electrons thereof.

4. A metal complex according to claim 3 wherein:
when x is 2, 1 and x' are both zero, M is in the +4 formal oxidation state, and X is independently each occurrence methyl, benzyl, or halide;
when x and l are zero, x' is one, and M is in the +4 formal oxidation state, X' is a 1,4-butadienyl group that forms a metallocyclopentene ring with M,
when x is 1, l and x' are zero, M is in the +3 formal oxidation state, and X is 2-(N,N-dimethylamino)benzyl; or
when x and x' are 0, l is 1, M is in the +2 formal oxidation state, and L is 1,4-diphenyl-1,3-butadiene or 1,3-pentadiene.

5. A metal complex according to claim 1 which is selected from the group consisting of:
(t-butylamido)dimethyl(1H-cyclopenta[1]-phenanthreneyl)silanetitanium(II) 1,4-diphenyl-1,3-butadiene,
(t-butylamido)dimethyl(1H-cyclopenta[1]-phenanthreneyl)silanetitanium(II) 1,3-pentadiene,
(t-butylamido)dimethyl(1H-cyclopenta[1]-phenanthreneyl)silanetitanium(III) 2-(N,N-dimethylamino)benzyl,
(t-butylamido)dimethyl(1H-cyclopenta[1]-phenanthreneyl)silanetitanium(IV) dichloride,
(t-butylamido)dimethyl(1H-cyclopenta[1]-phenanthreneyl)silanetitanium(IV) dimethyl,
(t-butylamido)dimethyl(1H-cyclopenta[1]-phenanthreneyl)silanetitanium(IV) dibenzyl,
(isopropylamido)dimethyl(1H-cyclopenta[1]-phenanthreneyl)silanetitanium(II) 1,4-diphenyl-1,3-butadiene,
(isoproptylamido)dimethyl(1H-cyclopenta[1]-phenanthreneyl)silanetitanium(II) 1,3-pentadiene,
(isopropylamido)dimethyl(1H-cyclopenta[1]-phenanthreneyl)silanetitanium(III) 2-(N,N-dimethylamino)benzyl,
(isopropylamido)dimethyl(1H-cyclopenta[1]-phenanthreneyl)silanetitanium(IV) dichloride,
(isopropylamido)dimethyl(1H-cyclopenta[1]-phenanthreneyl)silanetitanium(IV) dimethyl,
(isopropylamido)dimethyl(1H-cyclopenta[1]-phenanthreneyl)silanetitanium(IV) dibenzyl,
(benzylamido)dimethyl(1H-cyclopenta[1]-phenanthreneyl)silanetitanium(II) 1,4-diphenyl-1,3-butadiene,
(benzylamido)dimethyl(1H-cyclopenta[1]-phenanthreneyl)silanetitanium(II) 1,3-pentadiene,
(benzylamido)dimethyl(1H-cyclopenta[1]-phenanthreneyl)silanetitanium(III) 2-(N,N-dimethylamino)benzyl,
(benzylamido)dimethyl(; H-cyclopenta[1]-phenanthreneyl)silanetitanium(IV) dichloride,
(benzylamido)dimethyl(1H-cyclopenta[1]-phenanthreneyl)silanetitanium(IV) dimethyl,
(benzylamido)dimethyl(1H-cyclopenta[1]-phenanthreneyl)silanetitanium(IV) dibenzyl,
(cyclohexylamido)dimethyl(1H-cyclopenta[1]-phenanthreneyl)silanetitanium(II) 1,4-diphenyl-1,3-butadiene,
(cyclohexylamido)dimethyl(1H-cyclopenta[1]-phenanthreneyl)silanetitanium(II) 1,3-pentadiene,
(cyclohexylamido)dimethyl(1H-cyclopenta[1]-phenanthreneyl)silanetitanium(III) 2-(N,N-dimethylamino)benzyl,
(cyclohexylamido)dimethyl(1H-cyclopenta[1]-phenanthreneyl)silanetitanium(IV) dichloride, (cyclohexylamido)dimethyl(1H-cyclopenta[l]-phenanthreneyl)silanetitanium(IV) dimethyl,
(cyclohexylamido)dimethyl(1H-cyclopenta[l]-phenanthreneyl)silanetitanium(IV) dibenzyl,
cyclododecylamido)dimethyl(1H-cyclopenta[l]-phenanthreneyl)silanetitanium(II) 1,4-diphenyl-1,3-butadiene,
(cyclododecylamido)dimethyl(1H-cyclopenta[l]-phenanthreneyl)silanetitanium(II) 1,3-pentadiene,
(cyclododecylamido)dimethyl(1H-cyclopenta[l]-phenanthreneyl)silanetitanium(III) 2-(N,N-dimethylamino)benzyl,
(cyclododecylamido)dimethyl(1H-cyclopenta[l]-phenanthreneyl)silanetitanium(IV) dichloride,
(cyclododecylamido)dimethyl(1H-cyclopenta[l]-phenanthreneyl)silanetitanium(IV) dimethyl,
(cyclododecylamido)dimethyl(1H-cyclopenta[l]-phenanthreneyl)silanetitanium(IV) dibenzyl,
(t-butylamido)dimethyl(1-methyl-1H-cyclopenta[l]-phenanthreneyl)silanetitanium(II) 1,4-diphenyl-1,3-butadiene,
(t-butylamido)dimethyl(1-methyl-1H-cyclopenta[l]-phenanthreneyl)silanetitanium(II) 1,3-pentadiene,
(t-butylamido)dimethyl(1-methyl-1H-cyclopenta[l]-phenanthreneyl)silanetitanium(III) 2-(N,N-dimethylamino)benzyl,
(t-butylamido)dimethyl(1-methyl-1H-cyclopenta[l]-phenanthreneyl)silanetitanium(IV) dichloride,
(t-butylamido)dimethyl(1-methyl-1H-cyclopenta[l]-phenanthreneyl)silanetitanium(IV) dimethyl,
(t-butylamido)dimethyl(1-methyl-1H-cyclopenta[l]-phenanthreneyl)silanetitanium(IV) dibenzyl,
(isopropylamido)dimethyl(1-methyl-1H-cyclopenta[l]-phenanthreneyl)silanetitanium(II) 1,4-diphenyl-1,3-butadiene,
(isoproptylamido)dimethyl(1-methyl-1H-cyclopenta[l]-phenanthreneyl)silanetitanium(II) 1,3-pentadiene,
(isopropylamido)dimethyl(1-methyl-1H-cyclopenta[l]-phenanthreneyl)silanetitanium(III) 2-(N,N-dimethylamino)benzyl, isopropylamido)dimethyl(1-methyl-1H-cyclopenta[l]-phenanthreneyl)silanetitanium (IV) dichloride,
(isopropylamido)dimethyl(1-methyl-1H-cyclopenta[l]-phenanthreneyl)silanetitanium(IV) dimethyl,
(isopropylamido)dimethyl(1-methyl-1H-cyclopenta[l]-phenanthreneyl)silanetitanium(IV) dibenzyl,
(benzylamido)dimethyl(1-methyl-1H-cyclopenta[l]-phenanthreneyl)silanetitanium(II) 1,4-diphenyl-1,3-butadiene,
(benzylamido)dimethyl(1-methyl-1H-cyclopenta[l]-phenanthreneyl)silanetitanium(II) 1,3-pentadiene,
(benzylamido)dimethyl(1-methyl-1H-cyclopenta[l]-phenanthreneyl)silanetitanium(III) 2-(N,N-dimethylamino)benzyl,
(benzylamido)dimethyl(1-methyl-1H-cyclopenta[l]-phenanthreneyl)silanetitanium(IV) dichloride,
(benzylamido)dimethyl(1-methyl-1H-cyclopenta[l]-phenanthreneyl)silanetitanium(IV) dimethyl,
(benzylamido)dimethyl(1-methyl-1H-cyclopenta[l]-phenanthreneyl)silanetitanium(IV) dibenzyl,
(cyclohexylamido)dimethyl(1-methyl-1H-cyclopenta[l]-phenanthreneyl)silanetitanium(II) 1,4-diphenyl-1,3-butadiene,
(cyclohexylamido)dimethyl(1-methyl-1H-cyclopenta[l]-phenanthreneyl)silanetitanium(II) 1,3-pentadiene,
(cyclohexylamido)dimethyl(1-methyl-1H-cyclopenta[l]-phenanthreneyl)silanetitanium(III) 2-(N,N-dimethylamino)benzyl,
(cyclohexylamido)dimethyl(1-methyl-1H-cyclopenta[l]-phenanthreneyl)silanetitanium(IV) dichloride,
(cyclohexylamido)dimethyl(1-methyl-1H-cyclopenta[l]-phenanthreneyl)silanetitanium(IV) dimethyl,
(cyclohexylamido)dimethyl(1-methyl-1H-cyclopenta[l]-phenanthreneyl)silanetitanium(IV) dibenzyl,
cyclododecylamido)dimethyl(1-methyl-1H-cyclopenta[l]-phenanthreneyl)silanetitanium(II) 1,4-diphenyl-1,3-butadiene,
(cyclododecylamido)dimethyl(1-methyl-1H-cyclopenta[l]-phenanthreneyl)silanetitanium(II) 1,3-pentadiene,
(cyclododecylamido)dimethyl(1-methyl-1H-cyclopenta[l]-phenanthreneyl)silanetitanium(III) 2-(N,N-dimethylamino)benzyl,
(cyclododecylamido)dimethyl(1-methyl-1H-cyclopenta[l]-phenanthreneyl)silanetitanium(IV) dichloride,
(cyclododecylamido)dimethyl(1-methyl-1H-cyclopenta[l]-phenanthreneyl)silanetitanium(IV) dimethyl,
(cyclododecylamido)dimethyl(1-methyl-1H-cyclopenta[l]-phenanthreneyl)silanetitanium(IV) dibenzyl,
(t-butylamido)dimethyl(1,3-dimethyl-1H-cyclopenta[l]-phenanthreneyl)silanetitanium(II) 1,4-diphenyl-1,3-butadiene,
(t-butylamido)dimethyl(1,3-dimethyl-1H-cyclopenta[l]-phenanthreneyl)silanetitanium(II) 1,3-pentadiene,
(t-butylamido)dimethyl(1,3-dimethyl-1H-cyclopenta[l]-phenanthreneyl)silanetitanium(III) 2-(N,N-dimethylamino)benzyl,
(t-butylamido)dimethyl(1,3-dimethyl-1H-cyclopenta[l]-phenanthreneyl)silanetitanium(IV) dichloride,
(t-butylamido)dimethyl(1,3-dimethyl-1H-cyclopenta[l]-phenanthreneyl)silanetitanium(IV) dimethyl,
(t-butylamido)dimethyl(1,3-dimethyl-1H-cyclopenta[l]-phenanthreneyl)silanetitanium(IV) dibenzyl,
(isopropylamido)dimethyl(1,3-dimethyl-1H-cyclopenta[l]-phenanthreneyl)silanetitanium
(11)1,4-diphenyl-1,3-butadiene,
(isoproptylamido)dimethyl(1,3-dimethyl-1H-cyclopenta[l]-phenanthreneyl)silanetitanium(III) 1,3-pentadiene,
(isopropylamido)dimethyl(1,3-dimethyl-1H-cyclopenta[l]-phenanthreneyl)silanetitanium(III) 2-(N,N-dimethylamino)benzyl,
(isopropylamido)dimethyl(1,3-dimethyl-1H-cyclopenta[l]-phenanthreneyl)silanetitanium(IV) dichloride,
(isopropylamido)dimethyl(1,3-dimethyl-1H-cyclopenta[l]-phenanthreneyl)silanetitanium(IV) dimethyl,
(isopropylamido)dimethyl(1,3-dimethyl-1H-cyclopenta[l]-phenanthreneyl)silanetitanium(IV) dibenzyl,
(benzylamido)dimethyl(1,3-dimethyl-1H-cyclopenta[l]-phenanthreneyl)silanetitanium(II) 1,4-diphenyl-1,3-butadiene, (benzylamido)dimethyl(1,3-dimethyl-1H-cyclopenta[l]-phenanthreneyl)silanetitanium(II) 1,3-pentadiene,
(benzylamido)dimethyl(1,3-dimethyl-1H-cyclopenta[l]-phenanthreneyl)silanetitanium(III) 2-(N,N-dimethylamino)benzyl,
(benzylamido)dimethyl(1,3-dimethyl-1H-cyclopenta[l]-phenanthreneyl)silanetitanium(IV) dichloride,
(benzylamido)dimethyl(1,3-dimethyl-1H-cyclopenta[l]-phenanthreneyl)silanetitanium(IV) dimethyl,
(benzylamido)dimethyl(1,3-dimethyl-1H-cyclopenta[l]-phenanthreneyl)silanetitanium(IV) dibenzyl,
(cyclohexylamido)dimethyl(1,3-dimethyl-1H-cyclopenta[l]-phenanthreneyl)silanetitanium
(11)1,4-diphenyl-1,3-butadiene,
(cyclohexylamido)dimethyl(1,3-dimethyl-1H-cyclopenta[l]-phenanthreneyl)silanetitanium(II) 1,3-pentadiene, (cyclohexylamido)dimethyl(1,3-dimethyl-1H-cyclopenta[1]-phenanthreneyl)silanetitanium(III) 2-(N,N-dimethylamino)benzyl,
(cyclohexylamido)dimethyl(1,3-dimethyl-1H-cyclopenta[1]-phenanthreneyl)silanetitanium(IV) dichloride,
(cyclohexylamido)dimethyl(1,3-dimethyl-1H-cyclopenta[1]-phenanthreneyl)silanetitanium(IV) dimethyl,
(cyclohexylamido)dimethyl(1,3-dimethyl-1H-cyclopenta[1]-phenanthreneyl)silanetitanium(IV) dibenzyl, cyclododecylamido)dimethyl(1,3-dimethyl-1H-cyclopenta[1]-phenanthreneyl)silanetitanium (1)1,4-diphenyl-1,3-butadiene,
(cyclododecylamido)dimethyl(1,3-dimethyl-1H-cyclopenta[1]-phenanthreneyl)silanetitanium(II) 1,3-pentadiene,
(cyclododecylamido)dimethyl(1,3-dimethyl-1H-cyclopenta[1]-phenanthreneyl)silanetitanium(III) 2-(N,N-dimethylamino)benzyl,
(cyclododecylamido)dimethyl(1,3-dimethyl-1H-cyclopenta[1]-phenanthreneyl)silanetitanium(IV) dichloride,
(cyclododecylamido)dimethyl(1,3-dimethyl-1H-cyclopenta[1]-phenanthreneyl)silanetitanium(IV) dimethyl, and
(cyclododecylamido)dimethyl(1,3-dimethyl-1H-cyclopenta[1]-phenanthreneyl)silanetitanium(IV) dibenzyl.

6. A catalyst for olefin polymerization comprising:
A. 1) a metal complex of claim 1, and
2) an activating cocatalyst,
the molar ratio of 1) to 2) being from 1:10,000 to 100:1, or
B. the reaction product formed by converting a metal complex of claim 1 to an active catalyst by use of an activating technique.

7. The olefin polymerization catalyst of claim 6 wherein the activating cocatalyst comprises trispentafluorophenylborane.

8. The olefin polymerization catalyst of claim 7 wherein the activating cocatalyst comprises an alumoxane and trispentafluorophenylborane in a molar ratio from 1:1 to 5:1.

* * * * *